United States Patent [19]

Mark et al.

[11] Patent Number: 4,560,808

[45] Date of Patent: Dec. 24, 1985

[54] PROCESS FOR PRODUCTION OF DIHYDRIC PHENOLS

[75] Inventors: Victor Mark, Evansville; Charles V. Hedges, Mt. Vernon, both of Ind.

[73] Assignee: General Electric Company, Mt. Vernon, Ind.

[21] Appl. No.: 688,377

[22] Filed: Jan. 2, 1985

[51] Int. Cl.$^4$ .............................................. C07C 39/16
[52] U.S. Cl. ................................... 568/722; 568/53; 568/58; 568/333; 568/638
[58] Field of Search ............... 568/722, 723, 638, 333, 568/337, 58

[56] References Cited

U.S. PATENT DOCUMENTS

| | | | |
|---|---|---|---|
| 1,976,732 | 10/1934 | Johnson | 568/53 |
| 2,488,134 | 11/1949 | Mikeska et al. | 568/722 |
| 2,597,717 | 5/1952 | Faith | 568/722 |
| 3,000,853 | 9/1961 | Haven | 568/333 |
| 3,053,803 | 9/1962 | Jaffe et al. | 568/722 |
| 3,264,357 | 8/1966 | Webb et al. | 568/722 |
| 3,711,559 | 1/1973 | Ensor | 568/722 |
| 4,024,106 | 5/1977 | Mader | 568/333 |

FOREIGN PATENT DOCUMENTS

| | | | |
|---|---|---|---|
| 0072489 | 2/1983 | European Pat. Off. | 568/53 |
| 0077028 | 7/1978 | Japan | 568/638 |
| 485103 | 12/1975 | U.S.S.R. | 568/722 |

*Primary Examiner*—Werren B. Lone
*Attorney, Agent, or Firm*—Myron B. Kapustij; Martin B. Barancik

[57] ABSTRACT

A transalkylation process for the preparation of dihydric phenols comprising reacting, in the presence of an acid or base catalyst, at least one mole of an aromatic monohydroxy compound such as a phenol with at least one mole of an aromatic dihydroxy compound such as a dihydric phenol, thereby forming at least one dihydric phenol which is different than said aromatic dihydroxy compound.

19 Claims, 1 Drawing Figure

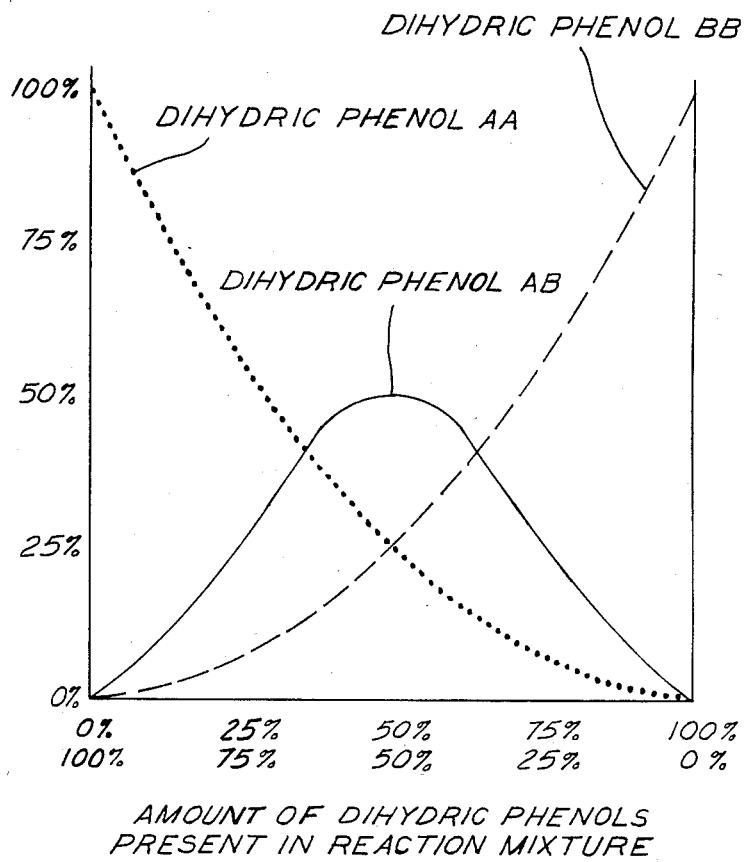
AMOUNT OF DIHYDRIC PHENOLS
PRESENT IN REACTION MIXTURE

PROCESS FOR PRODUCTION OF DIHYDRIC PHENOLS

BACKGROUND OF THE INVENTION

It is known to prepare dihydric phenols by condensing carbonyl compounds, such as aldehydes and ketones, with aromatic hydroxy compounds such as monohydric phenols under the influence of alkaline or acidic condensation catalysts. However, this reaction, particularly when an acid catalyst is employed, suffers from the disadvantages of relatively low yields of the dihydric phenol and the formation of undesirable by-products. Thus, for example, the reaction of phenol with formaldehyde in the presence of dilute mineral acids produces not only 4,4'-dihydroxydiphenyl methane but also a number of other isomers, particularly the 2,2'-dihydroxydiphenyl methane and the 2,4'-dihydroxydiphenyl methane, as well as resinous polycondensation products of the Novolak type. The formation of these resinous by-products can be retarded by either using a large excess of phenol or carrying out the reaction in a homogeneous solution in dilute mineral acid. However, even at best the yield of 4,4'-dihydroxydiphenyl methane has been reported by workers in the art as being only about 35%, and that of all isomers as being 70%, calculated on phenol.

There thus exists a need for a process for the preparation of dihydric phenols, particularly unsymmetrical dihydric phenols, which are substantially free of undesirable byproducts, such as resinous byproducts, and which yields the desired dihydric phenols in relatively large amounts. It is an object of the instant invention to provide such a process.

BRIEF DESCRIPTION OF THE FIGURE

The FIGURE shows the statistical distribution at equilibrium conditions of the dihydric phenols in mole percent.

SUMMARY OF THE INVENTION

The instant invention relates to a process for the preparation of dihydric phenols, including unsymmetrical dihydric phenols, comprising the reaction of a dihydroxy aromatic compound with a monohydroxy aromatic compound in the presence of a base or acid catalyst.

DETAILED DESCRIPTION OF THE INVENTION

It has been discovered that dihydric phenols, both unsymmetrical dihydric phenols and symmetrical dihydric phenols, may be readily prepared by the reaction of an aromatic dihydroxy compound with and aromatic monohydroxy compound in the presence of a catalyst selected from a base catalyst or an acid catalyst. The instant process may be represented by the following general reaction scheme:

I.
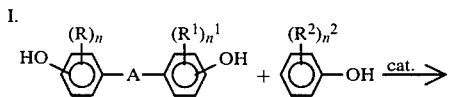

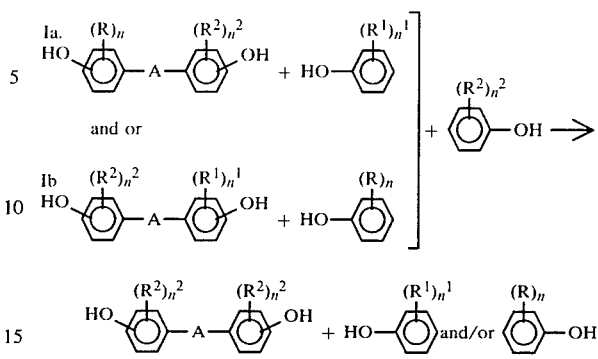

wherein:

$R$, $R^1$ and $R^2$ are independently selected from halogen, monovalent hydrocarbon, monovalent hydrocarbonoxy, and monovalent halogen substituted hydrocarbon radicals;

$n$, $n^1$ and $n^2$ are independently selected from integers having a value of from 0 to 4 inclusive; and A is a divalent radical selected from divalent hydrocarbon radicals, the —O— radical, the

radical, and the —S— radical;

The monovalent hydrocarbon radicals represented by $R$, $R^1$ and $R^2$ are selected from alkyl radicals, cycloalkyl radicals, aryl radicals, alkaryl radicals, and aralkyl radicals.

The alkyl radicals may be either branched or straight chain alkyl radicals. The preferred alkyl radicals are those containing from 1 to about 8 carbon atoms (e.g., methyl, ethyl, propyl, isopropyl, and butyl).

The preferred cycloalkyl radicals are those containing from 4 to about 8 ring carbon atoms (e.g., cyclobutyl, cyclohexyl, and methylcyclohexyl).

The preferred aryl radicals are those containing from 6 to 12 ring carbon atoms. These preferred aryl radicals are phenyl, biphenyl and naphthyl.

The preferred aralkyl and alkaryl radicals are those containing from 7 to about 14 carbon atoms.

The monovalent hydrocarbonoxy radicals represented by $R$, $R^1$ and $R^2$ may be represented by the formula —$OR^3$ wherein $R^3$ is a monovalent hydrocarbon radical as described hereinafore. The preferred hydrocarbonoxy radicals are the alkoxy and aryloxy radicals.

The monovalent halogen substituted hydrocarbon radicals may be represented by the formula $(X)_y$—$R^3$— wherein $R^3$ is a monovalent hydrocarbon radical, X is fluorine, chlorine or bromine, and y is an integer having a value of from 1 to about 4. Preferred radicals of this type are the fluoroalkyl radicals, particularly the perfluoroalkyl radicals.

The divalent hydrocarbon radicals represented by A are selected from alkylene radicals, alkylidene radicals, cycloalkylene radicals and cycloalkylidene radicals. The preferred alkylene radicals are those containing from 2 to about 30 carbon atoms. The preferred alkylidene radicals are those containing from 1 to about 30 carbon atoms. The preferred cycloalkylene and cycloalkylidene radicals represented by A are those containing from 4 to about 16 ring carbon atoms.

The product distribution in reaction I, i.e., the products Ia or Ib, can be generally controlled to a certain extent by the selection of the catalyst, either using a base catalyst or an acid catalyst; by selection of the substituent groups present on the aromatic nuclear residues of the aromatic dihydroxy reactants; controlling the proportions of the reactants used; and selective removal, as for example by distillation, from the reaction mixture of the lower boiling monophenol coproduct; and combinations thereof.

Thus, for example, if the catalyst used is an acid catalyst and R in reaction scheme I is an electron releasing group or groups, then the formation of products Ib can generally be enhanced. If a base catalyst is used, and if $R^1$ is an electron withdrawing group or groups, then the formation of products Ia can generally be enhanced.

Some illustrative non-limiting examples of the dihydric phenol reactants which may be utilized in the instant process include:
2,2-bis(4-hydroxyphenyl)propane(bisphenol-A);
2,2-bis(3,5-dimethyl-4-hydroxyphenyl)propane;
1,1-bis(4-hydroxyphenyl)decane;
1,1-bis(3,5-dimethyl-4-hydroxyphenyl)dodecane;
1,1-bis(3,5-dibromo-4-hydroxyphenyl)cyclohexane;
2,2-bis(3,5-dibromo-4-hydroxyphenyl)propane;
2,2-bis(3-methyl-5-bromo-4-hydroxyphenyl)propane;
1,1-bis(4-hydroxyphenyl)cyclohexane;
1,6-bis(4-hydroxyphenyl)hexane;
1,1-bis(4-hydroxyphenyl)cyclododecane;
2,2-bis(3,5-dichloro-4-hydroxyphenyl)propane;
2,2-bis(3,5-dibromo-4-hydroxyphenyl)propane;
2,2-(3-hydroxyphenyl)(4'-hydroxyphenyl)propane;
1,1-bis(3,5-dimethyl-4-hydroxyphenyl)cyclododecane;
2,2-(4,4'-dihydroxy-3-methyl-diphenyl)propane;
1,6-bis(3-chloro-4-hydroxyphenyl)hexane;
2,2-(4,4'-dihydroxy-3-chloro-diphenyl)propane;
bis(3-chloro-4-hydroxyphenyl)sulfide; and
bis(4-hydroxyphenyl)ether.

Some illustrative non-limiting examples of the monohydric phenol reactants which may be used in the process of the instant invention include:
phenol;
o-chlorophenol;
m-cresol;
p-cresol;
2,6-xylenol;
o-bromophenol;
2,3,6-trimethylphenol;
2,6-diethylphenol;
2-chloro-6-methylphenol;
2,3-dimethyl-6-ethylphenol;
o-cresol;
o-fluorophenol;
2,3-difluorophenol;
2,6-dichlorophenol;
2,6-dibromophenol;
2-chloro-6-fluorophenol;
2-chloro-6-methylphenol;
2,3,5,6-tetramethylphenol;
guaiacol; and
2,3,5,6-tetrachlorophenol.

The instant process, which may be characterized as involving an exchange reaction, is quite general and a large number of different dihydric phenols undergo this acid or base catalyzed exchange reaction with large numbers of diverse monohydric aromatic compounds or monophenols to yield dihydric phenol products which are different than the starting dihydric phenol reactants. The instant exchange reaction may be best illustrated by the use of symbols such as letters A, B and C to represent the monophenols; and the double letters AA, AB, AC, BB, BC and CC to represent the dihydric phenols, said double letters indicating the nature or structure of the two phenolic moieties forming the dihydric phenol.

The instant exchange reaction involving three different dihydric phenols of the type represented by the aforesaid double letters and the monophenols of the type represented by the aforesaid single letters, can be represented as a triangle whose apices are dihydric phenols comprised of two identical phenolic moieties, with the mid-points between the apices representing unsymmetrical dihydric phenols which are comprised of two different phenolic moieties derived from two different monophenols.

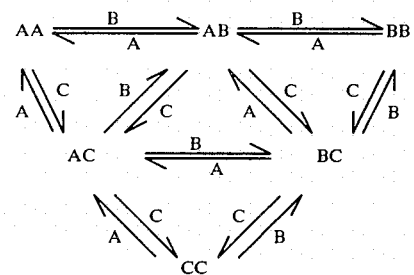

As illustrated in this diagram the reaction of a symmetrical dihydric phenol represented by AA, BB or CC (e.g., bisphenol-A, 2,2-bis(3,5-dimethyl-4-hydroxyphenyl)propane, 2,2-bis(3,5-dibromo-4-hydroxyphenyl)propane, etc.) with a monophenol which does not contain one of the phenolic moieties of the symmetrical dihydric phenol (such as B or C with dihydric phenol AA, or A or C with dihydric phenol BB, or A or B with dihydric phenol CC) yields unsymmetrical dihydric phenols such as BC, AC, or AB (e.g., 2,2-(4,4'-dihydroxy-3,5-dibromodiphenyl)propane, 2,2-(4,4'-dihydroxy-3,5-dimethyldiphenyl)propane, etc.).

The simplest systems are represented by the apices of the triangle as, for example, when a symmetrical dihydric phenol such as AA reacts with a monophenol such as B to yield the unsymmetrical dihydric phenol AB, in a reaction process wherein the constituent phenol A is liberated from the dihydric phenol AA. As the reaction porgresses, more of the monophenol B is consumed and more monophenol A is liberated. When the monophenols A and B are of generally similar reactivity as, for example, in a homologous series such as methylphenol and ethylphenol, then the unsymmetrical or "mixed" dihydric phenol AB can react with similar ease with either A or B. If dihydric phenol AB reacts with A, the original symmetrical dihydric phenol AA is reformed. If it reacts with B, however, then a new symmetrical dihydric phenol, namely BB, is produced. In other words, the three dihydric phenols AA, AB and BB are in an equilibrium and their relative proportions are determined by their relative reactivities or selectivities and the reactivities of the monophenol reactants, and by their molecular proportions at the beginning of the reaction, i.e., the AA to B mole ratios present in the reaction mixture.

For the theoretical case where the reactivities of A and B are identical, and the reactivities of AA, AB, and BB are identical, the equilibrium conditions may be represented by the FIGURE which represents the statistical distribution for an ideally random case.

In the FIGURE the dotted line represents dihydric phenol AA, the dashed line represents dihydric phenol BB, and the solid line represents dihydric phenol AB.

The FIGURE also illustrates that the same equilibrium mixture is attained when approached by either the reaction of BB with A or by the reaction of AA with B. At equilibrium the reaction mixture contains 25 mole % AA, 25 mole % BB, and 50 mole % AB, as well as 50 mole % A and 50 mole % B if the original mixture was equimolar in monophenol and dihydric phenol.

In practice the equilibrium concentrations can be altered, even in the case of reactants of generally similar reactivity, by several means such as, for example, by increasing the molar concentrations of one of the reactants or by disturbing the equilibrium by the selective removal of one of the products formed during the reaction from the reaction mixture.

As an illustration of the first means a gradual increase in the original concentration of B in its reaction with AA will yield increasingly more AB, and eventually more BB, than the 25 mole % shown in the diagram. A similar result obtains when during the course of the reaction A is gradually and continuosly removed from the reaction mixture as it is formed, as for example by distillation. In this case the effective concentration of B is increased, thereby resulting in the formation of more BB than is illustrated by the diagram.

An increase in the concentration of the dihydric phenol BB also results when the reactants are of dissimilar reactivities, for example in the case where B is more reactive than A.

When reacting an unsymmetrical dihydric phenol such as AB with a monophenol such as C, two new unsymmetrical dihydric phenol products can be produced utilizing the instant exchange reaction. These new dihydric phenols are AC and BC, as illustrated in the midsection of the triangular diagram. On further reaction with monophenol C both of these dihydric phenols AC and BC produce a new symmetrical dihydric phenol CC.

The proportion of the monophenol reactant relative to the dihydric phenol reactant in the reaction mixture is generally not a narrowly critical factor. For a theoretically complete reaction of the type illustrated by Formulae Ia and/or IB one mole of a monophenol reactant is required for each mole of the dihydric phenol reactant. However, an excess of the monophenol reactant may be used.

In order for the reaction illustrated by Formula I to proceed to substantial completion, that is beyond the equilibrium stage, thereby resulting in the formation of a new dihydric phenol product which is different from the dihydric phenol reactant, it is generally necessary to remove the monohydric phenol coproduct formed during the reaction from the reaction mixture. If this monohydric phenol coproduct is not removed from the reaction mixture it will tend to react with the new dihydric phenol product formed thereby forming the original dihydric phenol reactant as a product and the original monohydric phenol reactant as a coproduct. That is to say, this reaction is reversible and an equilibrium between the reactants and the products is established. Generally, it is preferable to remove the monohydric phenol coproduct from the reaction mixture as quickly as it is formed. One method of removing the monohydric phenol coproduct is by distilling it off as quickly as it is formed. In order to accomplish the distillation of this monohydric phenol coproduct without adversely affecting the production of the dihydric phenol product the monophenol coproduct must have a boiling point which is lower than the boiling points of the dihydric phenol reactant and the monophenol reactant. By appropriate selection of the reactants this situation may be readily achieved.

The process illustrated by Formula I, i.e., Ia and/or Ib, is particularly useful for the preparation of unsymmetrical dihydric phenols which usually are not readily available by conventional synthesis.

An illustrative non-limiting example of the preparation of an unsymmetrical dihydric phenol from a symmetrical dihydric phenol is the preparation of 2,2(4,4'-dihydroxy-3,5-dimethyldiphenyl)propane by reacting, in the presence of an acid catalyst, 2,6-xylenol with bisphenol-A. This reaction may be illustrated by the formula

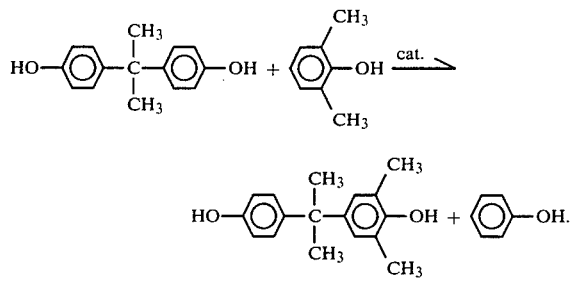

In the reaction the phenol coproduct has a lower boiling point than either of the dihydric phenols, i.e., either the dihydric phenol reactant or the dihydric phenol product, or the xylenol reactant and may thus be readily removed from the reaction mixture as soon as it is formed until the maximum concentration of the unsymmetrical dihydric phenol product is achieved. If it is the object to obtain this unsymmetrical dihydric phenol product the reaction must be stopped at this point, otherwise the unsymmetrical 2,2(4,4'-dihydroxy-3,5-dimethyldiphenyl)propane will react further with the xylenol to produce the new symmetrical dihydric phenol product 2,2-bis(3,5-dimethyl-4-hydroxyphenyl)propane in essentially quantitative yields in accordance with the following reaction

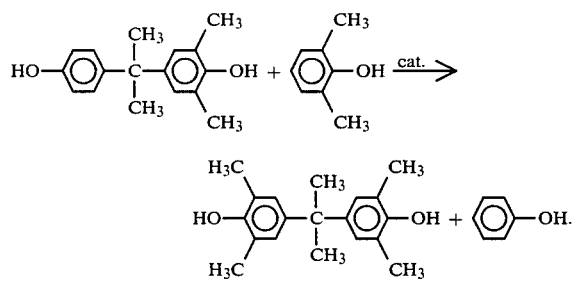

The advantage of the instant process resides in the fact that much fewer byproducts are formed than in any of the conventional dihydric phenol syntheses. These conventional dihydric phenol syntheses usually start with a carbonyl compound such as an aldehyde or a ketone, and a phenol, and an acid catalyst. These conventional syntheses result in byproducts formed from side reactions of the carbonyl compounds such as, for example, self-condensation, resulting in colored byproducts, and further reactions resulting in dihydric phenol related byproducts such as chromans, flavans, spiro-compounds, indane derivatives, and the like.

Since in its preferred embodiment the present exchange reaction utilizes a relatively pure dihydric phenol reactant it produces not only a dihydric phenol product which is different than the dihydric phenol reactant and which is substantially free of byproducts, but it also produces isomerically purer dihydric phenol products than conventional synthesis. For example, the 2,2(4,4'-dihydroxy-3,5-dimethyldiphenyl)propane discussed hereinafore is obtained as the essentially pure 4,4'-isomer, substantially free of the 2',4-isomer.

The instant transalkylation reaction is catalyzed by both acid catalysts and base catalysts. Acid catalyzed reaction conditions are generally preferred when both the dihydric phenol and monohydric phenol reactants are relatively electron rich, i.e., they contain substituent groups which are electron releasing, since the acid catalyst, which initiates the reaction, is electrophilic. Substituent groups which render the dihydric phenol and monohydric phenol reactants electron rich, and which are compatible with the acid catalysts, include hydrogen and electron releasing groups such as hydrocarbon, hydrocarbonoxy and hydroxy groups.

The acid catalysts include the protic and Lewis acids. The protic acids include the inorganic acids such as hydrochloric acid, hydrofluoric acid, hydrobromic acid, sulfuric acid, and phosphoric acid; and the strong organic acids such as the sulfonic acid phosphonic acids, e.g., methanesulfonic acid, toluene sulfonic acid, benzenesulfonic acid, methanephosphonic acid, and the like. Useful Lewis acids include borontrifluoride, stannic chloride, dialkyl tin oxide, and the like.

Exchange reactions catalyzed by strong bases are generally preferred when both the dihydric phenol and monohydric phenol reactants carry electronegative (electron withdrawing) substituent groups, since the base catalyst, which initiates the reaction, is nucleophilic. Examples of electronegative substituent groups suitable for the base catalyzed exchange reaction include the halogens such as chlorine, bromine, and fluorine, and the perfluoroalkyls such as trifluoromethyl.

Suitable base catalysts include the alkali and alkaline earth metal hydroxides, alkali metal carbonates and hydrogen carbonates, and the like. Some illustrative non-limiting examples of these base catalysts include sodium hydroxide, potassium hydroxide, barium hydroxide, calcium hydroxide, sodium hydrogen carbonate, sodium carbonate, potassium carbonate, and lithium hydroxide.

Although it is generally preferred to use an acid catalyst when the dihydric and/or monohydric phenol reactants contain electron releasing groups, and base catalysts when these reactants contain electron withdrawing groups, it is to be understood that it is possible to use either the acid or base catalysts with some dihydric phenol and/or monohydric phenol reactants.

The amount of catalyst employed in the instant process is a catalytic amount. By catalytic amount is meant an amount effective to promote or initiate the exchange reaction between the dihydric phenol and monohydric phenol reactants. In general this amount is in the range of from about 0.01 to about 10 weight percent, based on the weight of the dihydric phenol reactant present, preferably from about 0.1–5 weight %.

The temperature conditions at which the instant reaction proceeds generally range from below ambient temperatures, typically from about $-20°$ C., to above about $200°$ C. The temperature at which the reaction is carried out is, to a certain degree, dependent upon the reactants utilized. Thus, for example, with some reactants higher temperatures are required to make the reaction proceed than with other reactants. The lower limit of the temperature is thus a temperature which is effective for the reactants to coreact to form the dihydric phenol product. The upper temperature limit is generally controlled by the factor that it should be insufficient for the most volatile reactant to evaporate or be distilled off from the reaction mixture, or for the formation of undesirable byproducts.

The instant reaction process is particularly useful in the preparation of the 4,4'-isomers of the dihydric phenols, i.e., dihydric phenols represented by the general formulae

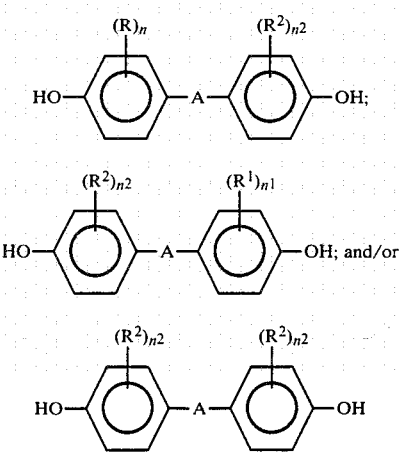

wherein R, $R^1$, $R^2$, A, n, $n^1$ and $n^2$ are as defined hereinafore.

DESCRIPTION OF THE PREFERRED EMBODIMENTS

The following examples are presented to more fully and clearly illustrate the instant invention and are intended to be exemplary and not limitative of the invention. Unless otherwise stated, all parts and percentages are by weight.

EXAMPLE 1

This example illustrates the preparation of 2,2-(4,4'-dihydroxy-3,5-dimethyldiphenyl)propane and 2,2-bis(3,5-dimethyl-4-hydroxyphenyl)propane from 2,2-bis(4-hydroxyphenyl)propane and 2,6-xylenol.

Into a warm slurry of 45.7 grams (0.2 mole) of 2,2-bis(4-hydroxyphenyl)propane in 244.2 grams (2.0 moles) of molten 2,6-xylenol there was gradually introduced, with stirring, at $55°$ C. dry hydrogen chloride gas. During the course of about 2 hours all of the 2,2-bis(4-hydroxyphenyl)propane was dissolved in the reaction mixture. The reaction was followed by sampling the reaction mixture at intervals and silylating the samples withdrawn from the reaction mixture with bis(trimethylsilyl)acetamide for gas chromatographic analysis. The reaction profile, as determined by gas chromatographic analysis of the samples removed from the reaction mixture, is set forth in Table I.

TABLE I

| | Dihydric phenols (relative mole %) | |
|---|---|---|
| | 2,2- | 2,2-bis- |

1:10. The dihydric phenol reactants, monohydric phenol reactants, dihydric phenol products, and monohydric phenol coproducts, as well as their gas chromatographic elution times, along with the catalysts employed, are set forth in Table II. The gas chromatographic reference compound is p-cumylphenol.

TABLE II

| | Reactants | | | | | |
|---|---|---|---|---|---|---|
| Example No. | Dihydric Phenol | GC minutes | GC of Reference (minutes) | Monohydric phenol | GC (min.) | Reaction Temp. (°C.) |
| 2 | 2,2-bis(4-hydroxyphenyl) propane | 17.83 | 13.96 | 2,3,6-trimethylphenol | 6.86 | 75 |
| 3 | " | 17.31 | 13.58 | o-cresol | 3.39 | 45 |
| 4 | 2,2-bis(3,5-dimethyl-4-hydroxyphenyl)propane | 19.67 | 13.59 | phenol | 2.47 | 25 |
| 5 | " | 19.67 | 13.58 | o-cresol | 3.41 | 25 |
| 6 | " | 19.48 | 13.41 | p-cresol | 3.55 | 25 |
| 7 | 2,2-bis(4-hydroxyphenyl)butane | 17.89 | 13.35 | 2,6-xylenol | 4.66 | 24 |
| 8 | 1,1-bis(4-hydroxyphenyl)ethane | 17.55 | 14.61 | " | 5.24 | 90 |
| 9 | bis(4-hydroxyphenyl)methane | 16.79 | 13.62 | " | 5.00 | 105 |
| 10 | 2,2-bis(3,5-dichloro-4-hydroxyphenyl)propane | 22.92 | 14.00 | " | 5.07 | 150 |
| 11 | bis(4-hydroxyphenyl)sulfide | 18.94 | 14.14 | " | 5.19 | 92 |

| | Products | | | | | |
|---|---|---|---|---|---|---|
| Example No. | Dihydric phenol | GC (min.) | Dihydric phenol | GC (min.) | Monohydric phenol | GC (min) | Catalyst |
| 2 | 2,2-(4,4'-dihydroxy-2,3,5-trimethyldiphenyl)propane | 19.07 | 2,2-bis(2,3,5-trimethyl-4-hydroxyphenyl)propane | 20.58 | phenol | 2.69 | methanesulfonic acid |
| 3 | 2,2-(4,4'-dihydroxy-3-methyldiphenyl)propane | 17.74 | 2,2-bis(3-methyl-4-hydroxyphenyl)propane | 18.11 | phenol | 2.44 | HCl |
| 4 | 2,2-(4,4'-dihydroxy-3,5-d-methylidiphenyl)propane | 18.58 | 2,2-bis(4-hydroxyphenyl) propane | 17.41 | 2,6-xylenol | 4.72 | methanesulfonic acid |
| 5 | 2,2-(4,4'-dihydroxy-3',3,5-trimethyldiphenyl)propane | 18.90 | 2,2-bis(3-methyl-4-hydroxyphenyl)propane | 18.10 | 2,6-xylenol 2,6-xylenol | 4.72 4.57 | methanesulfonic acid |
| 6 | 2,2-(2',4-dihydroxy-5',3,5-trimethyldiphenyl)propane | 17.73 | 2,2-bis(5-methyl-2-hydroxyphenyl)propane | 16.06 | phenol | 2.33 | methanesulfonic acid |
| 7 | 2,2-(4,4'-dihydroxy-3,5-dimethyldiphenyl)butane | 19.01 | 2,2-bis(3,5-dimethyl-4-hydroxyphenyl)butane | 19.98 | phenol | 2.74 | methanesulfonic acid |
| 8 | 1,1-(4,4'-dihydroxy-3,5-dimethyldiphenyl)ethane | 18.97 | 1,1-bis(3,5-dimethyl-4-hydroxyphenyl)ethane | 20.22 | phenol | 2.45 | methanesulfonic acid |
| 9 | (4,4'-dihydroxy-3,5-dimethyldiphenyl)methane | 18.39 | bis(3,5-dimethyl-4-hydroxyphenyl)methane | 19.82 | 2,6-dichlorophenol | 6.68 | methanesulfonic acid |
| 10 | 2,2-(4,4'-dihydroxy-3',5'-dihloro-3,5-dimethyldiphenyl)propane | 21.56 | 2,2-bis(3,5-dimethyl-4-hydroxyphenyl)propane | 20.24 | phenol | | methanesulfonic acid |
| 11 | (4,4'-dihydroxy-3,5-dimethyldiphenyl)sulfide | 20.46 | bis(3,5-dimethyl-4-hydroxyphenyl)sulfide | 21.93 | | 2.74 | methanesulfonic acid |

| Time (hrs.) | 2,2-bis-(4-hydroxyphenyl) propane | (4,4'-dihydroxy-3,5-dimethyldiphenyl) propane | (3,5-dimethyl-4-hydroxyphenyl) propane |
|---|---|---|---|
| 0 | 100 | 0 | 0 |
| 3 | 78.5 | 20 | 1.5 |
| 6 | 64.1 | 31.3 | 4.6 |
| 11 | 29.5 | 47.0 | 23.5 |

While the data indicate the essentially random equilibration of the reaction in about 11 hours, the equilibrium can be reached faster by using higher temperatures and/or by the selective removal of the phenol coproduct formed during the reaction. Due to the relative volatility of the hydrogen halides, the preferred acid catalysts used at higher temperatures are the less volatile sulfonic acids such as, for example, methanesulfonic acid, benzenesulfonic acid, and toluene sulfonic acid. Since methanesulfonic acid is liquid at room temperatures and has good solvent properties it can be used in a dual role as a catalyst/solvent at room temperatures or below room temperatures.

EXAMPLES 2-11

A variety of dihydric phenol products were prepared by the reaction of a variety of dihydric phenol reactants with monohydric phenol reactants using different acid catalysts. In these examples the molar ratio of dihydric phenol reactant to monohydric phenol reactant was

EXAMPLE 12

This example illustrates the base catalyzed preparation of 2,2-(4,4'-dihydroxy-3-methyldiphenyl)propane and 2,2-bis(3-methyl-4-hydroxyphenyl)propane from 2,2-bis(4-hydroxyphenyl)propane and o-cresol.

A reaction mixture consisting of 5.4 grams (0.05 mole) of o-cresol, 2.3 grams (0.01) of 2,2-bis(4-hydroxyphenyl)propane and 0.01 gram of sodium hydrogen carbonate was placed into a flask immersed in an oil bath and heated at 180° C. The reaction was followed by gas chromatographic analysis of samples removed at intervals from the reaction mixture. The reaction profile as monitored by gas chromatographic analysis, is set forth in Table III.

TABLE III

| | Dihydric phenols (relative mole %) | | |
|---|---|---|---|
| Time (hrs.) | 2,2-bis-(4-hydroxyphenyl) propane | 2,2-(4,4'-dihydroxy-3-methyldiphenyl) propane | 2,2-bis-(3-methyl-4-hydroxyphenyl) propane |
| 0 | 100 | 0 | 0 |
| 8 | 9.1 | 49.1 | 41.8 |
| 14 | 6.9 | 44.1 | 49.0 |

EXAMPLES 13–16

A variety of dihydric phenol products were prepared by the reaction of a variety of dihydric phenol reactants with monohydric phenol reactants using base catalysts. The dihydric phenol reactants, monohydric phenol reactants, dihydric phenol products, monohydric phenol coproducts, as well as their gas chromatographic elution times, along with the catalysts employed, are set forth in Table IV. The gas chromatopraphic reference is p-cumylphenol.

with at least one monohydroxy aromatic compound represented by the formula

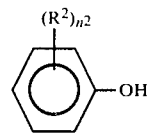

wherein

TABLE IV

| Example No. | Reactants Dihydric Phenol | GC (min.) | GC reference (min.) | Monohydric phenol | GC (min) | Reaction Temp. (°C.) |
|---|---|---|---|---|---|---|
| 13 | 2,2-bis(4-hydroxyphenyl) propane | 17.94 | 14.09 | 2,6-dichlorophenol | 6.86 | 180 |
| 14 | " | 17.74 | 13.98 | 2,6-xylenol | 4.96 | 180 |
| 15 | 2,2-bis(3,5-dichloro-4-hydroxyphenyl)propane | 23.04 | 14.02 | 2,6-xylenol | 5.05 | 190 |
| 16 | 2,2-bis(3,5-dibromo-4-hydroxyphenyl)propane | 25.43 | 13.71 | 2,6-dichlorophenol | 6.48 | 170 |

| Example No. | Products Dihydric phenol | GC (min.) | Dihydric phenol | GC (min.) | Monohydric Phenol | GC (min.) | Catalyst |
|---|---|---|---|---|---|---|---|
| 13 | 2,2-(4,4'-dihydroxy-3,5-dichlorodiphenyl)propane | 20.63 | 2,2-bis(3,5-dichloro-4-hydroxyphenyl)propane | 23.06 | phenol | 2.72 | NaHCO$_3$ |
| 14 | 2,2-(4,4'-dihydroxy-3,5-dimethyldiphenyl)propane | 19.00 | 2,2-bis(3,5-dimethyl-4-hydroxyphenyl)propane | 20.12 | phenol | 2.63 | NaHCO$_3$ |
| 15 | 2,2-(4,4-'dihydroxy-3,5-dichloro-3',5'-dimethyl-diphenyl)propane | 21.62 | 2,2-bis(3,5-dimethyl-4-hydroxyphenyl)propane | 20.16 | 2,6-dichlorophenol | 6.59 | NaHCO$_3$ |
| 16 | 2,2-(4,4'-dihydroxy-3,5-dichloro-3',5'-dibromo-diphenyl)propane | 23.96 | 2,2-bis(3,5-dichloro-4-hydroxyphenyl)propane | 22.64 | 2,6-dibromophenol | 9.24 | NaOH |

What is claimed is:

1. A process of preparing at least one dihydric phenol represented by the formulae

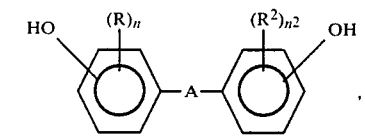

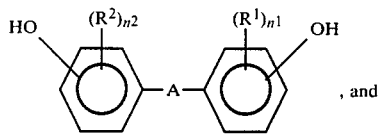
, and

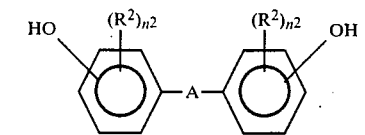

comprising reacting, in the presence of a catalytic amount of a catalyst selected from a base transalkylation catalyst or an acid catalyst selected from the protic acids and Lewis acids, at least one dihydroxy aromatic compound represented by the formula

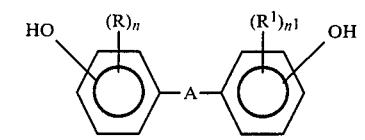

R is independently selected from halogen radicals, monovalent hydrocarbon radicals containing from 1 to about 14 carbon atoms, monovalent hydrocarbonoxy radicals containing from 1 to about 14 carbon atoms, and halogen substituted monovalent hydrocarbon radicals containing from 1 to about 14 carbon atoms, R$^1$ is independently selected from halogen radicals, monovalent hydrocarbon radicals containing from 1 to about 14 carbon atoms, monovalent hydrocarbonoxy radicals containing from 1 to about 14 carbon atoms, and halogen substituted monovalent hydrocarbon radicals containing from 1 to about 14 carbon atoms, R$^2$ is independently selected from halogen radicals, monovalent hydrocarbon radicals containing from 1 to about 14 carbon atoms, monovalent hydrocarbonoxy radicals containing from 1 to about 14 carbon atoms, and halogen substituted monovalent hydrocarbon radicals containing from 1 to about 14 carbon atoms, n, n$^1$ and n$^2$ are independently selected from integers having a value of from 0 to 4 inclusive, and A is selected from alkylene, cycloalkylene, alkylidene, cycloalkylidene,

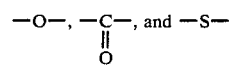

radicals.

2. The process of claim 1 wherein said monovalent hydrocarbon radicals represented by R$_2$ are selected from alkyl, cycloalkyl, aryl, aralkyl, and alkaryl radicals.

3. The process of claim 1 wherein said monovalent hydrocarbonoxy radicals represented by $R_2$ are selected from alkoxy and aryloxy radicals.

4. The process of claim 1 wherein A is selected from alkylene, alkylidene, cycloalkylene, and cycloalkylidene radicals.

5. The process of claim 1 wherein said monovalent hydrocarbon radicals represented by R and $R^1$ are selected from alkyl, cycloalkyl, aryl, aralkyl and alkaryl radicals.

6. The process of claim 1 wherein said catalyst is an acid catalyst.

7. The process of claim 6 wherein said acid is selected from mineral or protic acids.

8. The process of claim 6 wherein said acid is selected from the organic acids.

9. The process of claim 8 wherein said organic acids are selected from organic sulfonic acids and organic phosphonic acids.

10. The process of claim 1 wherein said catalyst is a base.

11. The process of claim 10 wherein said base is an inorganic base.

12. The process of claim 1 wherein said dihydroxy aromatic compound is a 4,4'-dihydric phenol.

13. The process of claim 12 wherein said 4,4'-dihydric phenol is bisphenol-A.

14. The process of claim 13 wherein said aromatic monohydroxy compound is 2,6-xylenol.

15. The process of claim 13 wherein said aromatic monohydroxy compound is cresol.

16. The process of claim 15 wherein said cresol is o-cresol.

17. The process of claim 1 wherein there is formed at least one dihydric phenol which is different from the dihydroxy aromatic compound.

18. The process of claim 17 wherein there are formed two different dihydric phenols which are different from each other and from the dihydroxy aromatic compound.

19. The porcess of claim 18 wherein said dihydric phenols which are prepared thereby comprise, together with the dihydroxy aromatic compound, a statistical mixture of three different dihydric phenols.

* * * * *